United States Patent [19]

Blum

[11] 4,072,703
[45] Feb. 7, 1978

[54] THIOL ESTERS OF HOMOCYSTEINE

[75] Inventor: Jean Blum, Courbevoie, France

[73] Assignee: Chimie & Biologie, France

[21] Appl. No.: 567,752

[22] Filed: Apr. 14, 1975

[30] Foreign Application Priority Data

Mar. 28, 1974 France .................... 74 10913

[51] Int. Cl.$^2$ .................. C07C 153/07; C07C 153/09; C07C 153/11
[52] U.S. Cl. ................. 260/455 R; 260/327 TH; 260/516; 260/534 S
[58] Field of Search ................................. 260/455 R

[56] References Cited

U.S. PATENT DOCUMENTS 2,935,529  5/1960  Wagner .................... 260/327 TH

OTHER PUBLICATIONS

J. Amer. Chem. Soc. vol. 85, pp. 1337–1341, (1963).
Chem. Abst. vol. 59, pp. 11659.
Dissertation Abst. vol. 25, pp. 4968 (1965).

Primary Examiner—Delbert R. Phillips

[57] ABSTRACT

ADT derivatives in free or salt forms, organic or mineral bases, in which the ADT derivatives contain the characteristic group —S—CH$_2$—CH$_2$—CH(NHR)—CO— in the cyclical form

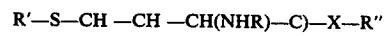

S—CH$_2$—CH$_2$—CH(NHR)——CO in which R represents an acyl group containing more than 4 carbon atoms and substituted when it is cynnamoyl, and the open form

R'—S—CH—CH—CH(NHR)—C)—X—R"

in which X is oxygen or sulfur, R' and R are the same or different and are selected from the group of hydrogen and acyl radicals, R" is hydrogen or a substituted alcoyl such that R" has at least 2 carbon atoms when X is oxygen, R is a lower acyl and R' is hydrogen.

5 Claims, No Drawings

THIOL ESTERS OF HOMOCYSTEINE

This is a continuation-in-part of my copending application Ser. No. 559,508, filed Mar. 21, 1975.

Amino-3 dihydrothiophenon-2 or homocystein thiolactone, hereinafter called ADT, was described by Du Vigneaud in 1935. It is prepared by dealkylation of methionine or another alcoyl homocystein by reduction by sodium in ammonia or hydriodic acid, followed by cyclization. Being relatively undeveloped, it is relatively costly because, being soluble in water, its isolation is delicate. Some N-acylated derivatives thereof are known, but the S-acyl homocysteins are unknown. The new reactions of the invention provide access, sometimes very economically, to numerous derivatives which are useful in therapeutics, cosmetology, photography, etc., and permit a more economic access to the known derivatives.

In the line of new industrial products, the invention relates, in the free form or in the form of basic or acidic organic or inorganic salts of the new ADT derivatives which include the characteristic grouping —S—CH$_2$—CH$_2$—CH(NHR)—CO, in which R represents a hydrogen or a C$_1$-C$_4$ acyl group. The structure of the compounds is either cyclical, according to formula

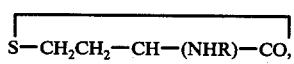
(A)

where R then has more than 4 carbons and it is substituted when it is a benzoyl or nicothinoyl and unsubstituted when it is a cinnamoyl, or open according to the formula (B) R'—S—CH$_2$—CH$_2$—CH(NHR)—CO—X—R", where X represents a sulfur or oxygen atom, R and R", being identical or different, represent hydrogen or acyl groups, R" representing a hydrogen or a possibly substituted alcoyl, wherein R" has at least 2 carbons when X is oxygen, R a benzoyl or lower (C$_1$-C$_5$) acyl and R' is hydrogen.

According to an embodiment of the invention, the compounds have the cyclical structure (A) and R is a radical selected of the following: p-chlorophenoxy-2 isobutyryl, pivaloyl, m-fluorobenzoyl, trimethoxy-3,4,5 benzoyl, succinoyl, p-chlorophenoxy acetyl, salicyloyl, acetyl-salicyloyl, thenoyl-2, chromone-2 carbonyl.

According to another embodiment, the compounds have the open structure (B) where X is oxygen, R' and R" hydrogen and R is one of the radicals identified in the preceding paragraph, plus the radicals nicotinoyl and propionyl.

According to another embodiment, the products have the open structure (B) where —XR" is a —OH and R and R', being identical or different, represent one of the following list of radicals: acetyl, propionyl, pivaloyl, succinoyl, benzoyl, m-fluorobenzoyl, trimethoxy-3,4,5 benzoyl, salicyloyl, acetylsalicyloyl, thenoyl-2, p-chlorophenoxy acetyl, p-chlorophenoxy-2 isobutyryl, nicotinoyl, chromone-2 carbonyl.

Another embodiment relates to the homologs of the products of the preceding paragraph in which R" becomes a methyl, ethyl, propyl or butyl radical.

The N-acyl ADT has been obtained by acylation of ADT in anhydrous media, and the N-acyl ADT of the invention thus can be obtained. The Yoshitomi Japanese Pat. No. 16712/62 refers to the acetylation of ADT in a bicarbonate solution with acetic anhydride.

The present invention also relates to new methods of N-acylation of ADT, where it is dissolved in an aqueous solvent, preferably water. A weak base, such as a bicarbonate, or a stronger one, such as sodium hydroxide, is added, but in a quantity calculated to avoid the hydrolysis of the thiolactone. An anhydride or an acid halide is added to this solution at a specific temperature of the reagent, optionally between −10° and ambient temperature, the acetic anhydride being excluded from the reagents used.

The invention furthermore relates to methods of S-acylation of the ADT's, either N-acylated or not, preferably in water, in two phases, namely, hydrolysis of the thiolactone and then acylation. The hydrolysis is accelerated when the pH and the temperature are elevated. These parameters are then lowered and an acid halide or anhydride is added. Sodium hydroxide is preferably used in excess and acylation is carried out between −10° and ambient temperature. At the end of the reaction the S-acyl homocystein is acidified and isolated. This technique makes it possible to arrive at compounds acylated identically or differently on sulfur and nitrogen atoms.

The invention also relates to methods for synthesis of S-acylated homocystein esters or thiolesters, which consist of saturating a solvent, such as an alcohol or reactive mercaptan, with anhydrous hydrochloric acid, dissolving therein the homocystein and letting the mixture stand, frequently at room temperature. The ester is isolated by evaporating off the solvent and by adding to the residue a bicarbonate solution to eliminate the residual homocystein.

The invention also relates to the methods of N- and S-acylation of homocystein esters and thiolesters. An acid anhydride or halide is added to the substratum in very mild alkaline medium, which either may be anhydrous, or aqueous at a moderated pH and cold temperature.

The invention also relates to the synthesis of S-acyl homocysteins, consisting of S-acylating a previously prepared ester, then hydrolyzing it by the action of an alkaline reagent, generally while cold.

The invention also relates to the preparation of N-acyl ADT and N and/or S-acylated homocysteins or unacylated homocysteins, from S-alcoyl homocysteins, which may or may not be N-acylated, preferably methionine or acetyl methionine. The reaction is initiated by dealkylating the substratum according to known methods; the solvent is evaporated without isolating the intermediate product, and the acylation is carried out successively on nitrogen and sulfur, in accordance with the previously described methods. If the dealkylation takes place in hydriodic acid, the evaporation residue is dissolved in water. The N-acylation is carried out at mild pH, and the pH is increased for the S-acylation. If the dealkylation is made with sodium in ammonia, the latter is evaporated and the residue dissolved in water. In order to identically N and S-acylate, the acylation is carried out directly. To N and S-aceylate differently, it is necessary to recycle in ADT by returning to the acid medium, return to the mild alkaline pH to N-acylate, then to the higher pH for the S-aceylation. These means are very economical because they avoid the delicate isolation of ADT; only the final product is to be isolated and frequently being insoluble, it precipitates directly.

The invention also relates to the methods of fabricating N,S-diacyl homocysteins which consist of N and then S-acylating the ADT without isolating the intermediate N-acyl ADT.

The invention likewise relates to medications for human or veterinary therapeutics which contain one or several of the new derivatives of the invention. It has been found that selected ones are relatively non-toxic and present various activities such as hepaprotective, cicatrizing, mucolytic, hypolipemiating, hypocholestrolemiating, vasoprotective, tranquilizing, platelets, anti-aggregating activities, etc. The homocystein support itself is atoxic and has interesting therapeutic properties which may be completed, synergized or modified by acid remnants, alcohols and mercaptans which themselves have therapeutic properties and whose products of the invention may serve as introduction factors to improve their pharmacological qualities or resolve problems of stability, solubility, time delaying effect, wall passage or others.

The products of this invention also have use as pharmaceutical compounds and can be used in forms for local, oral, parental, rectal administration in otorhinolaryngology and oththamology, such as pommades, solutions, milks, aerosols, pills, wafers, lozenges, gelatin-coated pills, chromules, syrups, capsules, drops, solutions for drinking or injections, all ready or to be prepared for use, cones, suppositories, enemas, containing in pure or in mixture condition one of the several derivatives of the invention.

Finally, the invention relates to the use of the new products of this invention for cosmetological applications and more specifically for skin, hair and nail care.

The following examples and tables, furnished in a non-limitative manner, illustrate the invention, but numerous other variants thereof can be visualized.

EXAMPLE 1

Method A

N-acetyl ADT Synthesis 1.535 grams ADT, HCl are dissolved in 10 cc caustic soda N and 1.1 cc acetic anhydride are added. The temperature rises from 22° to 29°, 10 minutes later 4 cc acetic acid are added and evaporated to dryness. This is taken up byaacetone, the salt is filtered and the filtrate evaporated. The product crystallizes by adding ether.

EXAMPLE 2

Method B

N-propionyl ADT

Example 1 is modified by replacing the calculated quantity of sodium hydroxide, often referred to as caustic soda, by an excess of sodium bicarbonate and the acetic anhydride by propionic anhydride.

EXAMPLE 3

Method C

N-p-chlorophenoxy-2 isobutytyl ADT

Dissolve 3.07 grams ADT, HCl in 20 cc dimethyl formamide. Heat until dissolution, cool to 50° and add 5.8 cc triethyl amine whose chlorohydrate precipitates, then 4.70 grams clofibryl chloride. The temperature rises to 70°. Heat for 2 minutes at 100° and cool, filter and add 80 cc water to the filtrate. An oil rapidly precipitates and crystallizes.

EXAMPLE 4

Method D

N-pivaloyl ADT

Example 2 is followed using pivaloyl chloride instead of propionic anhydride.

EXAMPLE 5

Method E

N,S-diacetyl homocystein 11.2 grams N-acetyl ADT are dissolved in 40 cc 14% caustic soda, and at 10° C 7.15 grams acetic anhydride are gently added. A few minutes later, this is acidified with 10% HCl, saturated with salt, the excess of which is filtered. This is extracted with methylene chloride, evaporated to dryness and taken up with ether. An oil subsequently precipitates and crystallizes.

EXAMPLE 6

Method F

N,S-diacetyl homocystein

The method is the same as in Example 5, but using ADT, HCl, whose molar quantity is tripled in caustic soda and doubled in acetic anhydride.

EXAMPLE 7

Method G

N,S-diacetyl homocystein

The procedure is the same as in Example 5, but replacing the anhydride with acetyl chloride and operating at 0° C.

EXAMPLE 8

Method H

N,S-diacetyl homocystein

According to Example 6, replacing the anhydride with acetyl chloride and operating at 0° C.

EXAMPLE 9

Method I

N,S-dibenzoyl homocystein

Dissolve 1.54 grams ADT, HCl in 20 cc caustic soda 2N and, at 10° add gently under agitation 2.9 grams benzoyl chloride. When the mixture is clear, add 10% HCl until pH 2. The product precipitates and crystallizes by freezing.

EXAMPLE 10

Method J

N-acetyl, S-benzoyl homocystein

Dissolve 1.59 grams N-acetyl ADT in 15 cc caustic soda 2N. At 10° gently add 1.45 grams benzoyl chloride. Return to 20° and when the mixture is clear, add 10% HCl until pH 2. The product rapidly precipitates and crystallizes.

EXAMPLE 11

Method K

N-acetyl, 5-benzoyl methyl homocysteinate

Introduce 3.28 grams N-acetyl methyl homocysteinate into 30 cc dry benzene and 2.06 grams triethyl amine. At 10° C, introduce 3.10 grams benzoyl chloride, let stand for 2 days and filter the salt. Wash the filter with diluted HCl, with bicarbonate, then with water. Dry the benzoic phase and evaporate 60 dryness, add a bicarbonate solution: the product crystallizes.

EXAMPLE 12

Method L

N-acetyl S-benzoyl methyl homocysteinate

The reagents of the preceding example are treated in 1N sodium hydroxide. The precipitate formed is immediately filtered and washed with water, producing only a low yield because of the hydrolysis.

EXAMPLE 13

Method M

N-acetyl, S-benzoyl methyl homocysteinate

In the preceding example, replacing the caustic soda with excess bicarbonate and allowing it to return to 20° C, the reaction is completed, and the hydrolysis avoided, leading to an excellent yield.

EXAMPLE 14

Method N

N-acetyl, Sp.chlorophenoxy-2 isobutyryl homocystein

The methyl ester is stirred for one hour in 1N sodium hydroxide solution, then acidify to pH 2 with 10% HCl. The product rapidly precipitates and crystallizes.

EXAMPLE 15

Method O

N-acetyl, S-benzoyl methyl homocystein

Dissolve 1.41 grams N-acetyl, S-benzoyl homocystein in 15 ml methyl alcohol saturated with anhydrous hydrochloric acid. Let stand for 12 hours and evaporate to dryness. Take up the residue again with 10% bicarbonate. By freezing, the product crystallizes.

EXAMPLE 16

Method P

N-acetyl-N-acetyl S-benzoyl homocysteinate,methyl homocysteinate

Equimolar quantities of N-acetyl, S-benzoyl homocystein and N-acetyl methyl homocysteinate are dissolved in hydrochloric dioxane. Let stand for one day and treat like in the preceding example.

EXAMPLE 17

Method R

N-acetyl, S-benzoyl homocystein

Dissolve 1.69 grams ADT, HCl in 22 cc 10% bicarbonate, and at 20° add 1.3 cc acetic anhydride. Allow to react for 10 minutes, cool to 15° C and add, by stirring, 1.41 grams benzoyl chloride. When the solution is clear, acidify to pH 2 with 10% HCl. The product precipitates and crystallizes.

EXAMPLE 18

Method Q

N-thenoyl-2 ADT 15 grams methionine are demethylized in 40% hydriodic acid according to known methods. The acid is evaporated to dryness under vacuum and the residue is taken up in 100 cc 10% sodium bicarbonate, and while being sure that the medium always is alkaline, add gently 14.65 grams thenoyl chloride at 15° C. The product solidifies in half an hour and it is filtered.

EXAMPLE 19

Method S

N-acetyl ADT 7.5 grams methionine are demethylized by sodium reduction in ammonia and the latter is evaporated off. For precaution, the residue of evaporation is destroyed with 5 cc alcohol, then neutralized to pH 2 with 10% HCl. Heat for ½ hour at 80° to cyclize and neutralize with excess sodium bicarbonate and at 20° C, add 6 cc acetic anyydride, then proceed with isolation like in Example 1.

EXAMPLE 20

Method T

N,S-diacetyl homocystein 7.5 grams methionine are likewise demethylized by sodium in ammonia which is evaporated off. After destruction of the residue with alcohol, dilute in water, cool to 15°–20° C and add 12 cc acetic anhydride. After a few minutes, acidify and isolate, as in Example 5.

EXAMPLE 21

Method U

N,S-dibenzoyl homocystein

According to Example 20, replacing the acetic anhydride with benzoyl chloride. At the end of the reaction, the product precipitates and crystallizes upon acidification.

EXAMPLE 22

Method V

N-acetyl, S-thenoyl-2 homocystein

The procedure is like Example 19 but N-acetyl ADT is not isolated. At this moment, 5 grams caustic soda in pellets are added to the mixture. Cool to 15° C and add 7.35 grams thenoyl chloride. When the mixture has become clear it is acidified at pH 2 and the product precipitates and crystallizes.

All products obtained according to methods A to V are in the form of white crystals, although this is not a characteristic for the invention. The following tabulation expands upon the examples by identification of the compounds and reactants as well as the method by which they are produced.

TABLE I

| | N-acyl ADT | | | | |
|---|---|---|---|---|---|
| Ex. No. Product | R | Method | Temp. ° C | Solvent of recrystal- ization | Melting Point Kofler Bank° C |
| 1.19 a | acetyl | A,S | 20-30 | eth.acetate | 112 |

TABLE I-continued
N-acyl ADT

| Ex. No. Product | R | Method | Temp. °C | Solvent of recrystalization | Melting Point Kofler Bank° C |
|---|---|---|---|---|---|
| 2 | propionyl | B | 20 | trichloroethylene | 96-6 |
| 3 & 28 | p.chlorophenoxy-2 isobutyryl | C,D | 50-100 | isopropanol | 103-4 |
| 4 | pivaloyl | D | 0-5 | water | 133 |
| 18 | thenoyl-2 | R | −30-15 | | |
| 23 | benzoyl | D | 10 | isopropanol | 148 |
| 24 | m.fluorobenzoyl | D | 10 | isopropanol | 143 |
| 25 | trimethoxy-3,4,5-benzoyl | D | 20 | ethanol | 172-3 |
| 26 | succinyl | B | 10 | water | 136-7 |
| 27 | p.chlorophenoxy-acetyl | D | 15-20 | isopropanol | 116 |
| 29 | nicotinoyl | D | −8 | water | 129 |
| 30 | salicyloyl (acetyl) | D | 10 | isopropanol | 142-3 |
| 31 | chromone-2 carbonyl | D | 10 | ethanol | 206 |

TABLE II
Open Form (B)

| Ex. No. Product | R'' (not indicated if H) R R' | Method (Temp. of the reaction ° C) | Recrystallization solvent | Melting Point banc Kofler ° C |
|---|---|---|---|---|
| 5,6,7,8,20 | Acetyl | E(10),F(10) G(0),H(0) | ethyl acet. or | 100 |
|  | Acetyl | T(−30 then 15) | dichloroethane | |
| 9, 21 | Benzoyl | I (10) | isopropanol | 172-3 |
|  | Benzoyl | U (−30 then 15°) | | |
| 10,17,41,34 | Acetyl | J(5-20),R(15) | water-ethanol | 153 |
|  | Benzoyl | N(room) V(−30 then 15) | | |
| 11,12,13 | Methyl | K(10),L(10) | | |
| 15,53 | Acetyl Benzoyl | M(10),0 (effected with H₂SO₄ at 20° | xylene | 89 |
| 14,36 | Acetyl p.Clphenoxy-2 isobutyryl | N(room) V(−30 then 15) | water-ethanol | 128-9 |
| 16 | N-acetyl homocysteinate methyl Acetyl Benzoyl | P(room) | xylene | 80 |
| 22,54 | Acetyl Thenoyl-2 | V(−30 then 15) J(10) | water-isopropanol | 152 |
| 32 | m.Fbenzoyl m.Fbenzoyl | I(10) | isopropanol | 148 |
| 33 | Acetyl m.F benzoyl | J(5-10) | water-isopr. | 154 |
| 35 | Acetyl o,Cl-phenoxy acetyl | J(10) | isopropanol | 130 |
| 37 | Methyl Acetyl Trimethoxy-3,4,5 benzoyl | M(10) | xylene | 114 |
| 38 | Methyl Acetyl p.Cl-phenoxy-acetyl | M(10) | isopropanol | 114 |
| 39 | Methyl Acetyl p.Cl-phenoxy-2 isobyryl | M(10) | Isopropanol | 92 |
| 40 | Methyl Acetyl Chromone-2 carbonyl | M910) | isopropanol | 141-2 |
| 42 | Ethyl Acetyl Benzoyl | O(room) | toluene-cyclohexane | 84 |
| 43 | Propyl-2 Acetyl Benzoyl | O(room) | toluene-cyclohexane | 86 |
| 44 | Butyl-2 Acetyl Benzoyl | O(room) | toluene petroleum ether | 63-4 |
| 45 | Ethyl | | toluene | |

TABLE II-continued

Open Form (B)

| Ex. No. Product | R" (not indicated if H) R R' | Method (Temp. of the reaction °C) | Recrystallization solvent | Melting Point banc Kofler °C |
|---|---|---|---|---|
| 46 | Acetyl Thenoyl-2 Ethyl | 0(room) | cyclohexane | 90 |
| 47 | Acetyl m.F-benzoyl | 0(room) | toluene-cyclohexane | 83 |
| 48 | Benzoyl Acetyl | J(10)start by hydrolyzing N-benzoyl ADT by heating to 90° | toluene | 120 |
| 49 | Methyl Benzoyl Acetyl | 0(room) | toluene | 142 |
| 50 | Acetyl malicyloyl | J(10)with acetyl salicyloyl chloride whose acetyl hydrolyzes | water-ethanol | 157-8 |
| 51 | Acetyl Pivaloyl | J(10-2) | water-ethanol | 163 |
| 52 | Methyl Acetyl Pivaloyl | 0(room) | water-ethanol | 84 |
|  | Acetyl | J(15) using succinic anhydride | water | 134 |

EXAMPLE 55

N-acetyl, S-benzoyl homocysteinate of Mg.

In order to obtain a molar solution of this salt, 1/200 mole of $MgCO_3$ are agitated for 15 minutes, with 1/100 mole N-acetyl, S-benzoyl homocystein, in 10 cc of water.

EXAMPLE 56

N-acetyl, S-p.Clphenoxy-2 isobutyrate of nicotinomethanol.

By operating as in the following Example 57, with the corresponding reagents, a molar solution of the salt is obtained.

EXAMPLE 57 dimethyl-amino ethanol N-acetyl, S-p. Clphenoxy acetyl homocysteinate.

The molar solution of the salt is obtained by dissolution in 10 cc of water, 1/100 mole of dimethyl amino ethanol and N-acetyl, S-pCl phenoxyacetyl homocystein, which originally were insoluble.

EXAMPLE 58

S-nicothinoyl ADT acetyl aspartate

By mixing acetyl aspartic acid and N-nicotinoyl ADT in equimolecular quantities at the rate of 1 mole per liter of water, the dissolution of the reagents and the formation of the salt are observed.

EXAMPLE 59

Oxy tetracycline N,S-diacetyl homocystainate.

Equimolecular quantities of N,S-diacetyl homocystein and the oxy tetracycline base are dissolved in methyl alcohol, and this is evaporated while cold under vacuum. A yellow powder, soluble in water, is obtained which melts at 125°.

The industrial interest of the products of the invention is illustrated by the following examples given without limitation; it being understood that the DL 50 determinations were made orally in the mouse.

Product 24 DL 50: 1.9 grams/kilogram. In the rabbit undergoing a hypercaloric regime, it reduces to 250 mg/kg the circulating lipid rate. In human therapeutics, the daily dose is 100 to 2000 mg/day.

Product 25: DL 0 above 2.5 grams/kg. From 400 mg/kg, notable sedation is observed, and at 1 g/kg meeting of animals then hypnosis is observed.

Product 26: DL 0 above 2 grams/kg. At 400 mg/kg it is very clearly mucolytic in the rat according to the test of chronic bronchitis with $SO_2$, by Auevauvillier. It is usable to treat respiratory ailments at the daily rate from 100 to 3000 mg/day.

Product 27: DL 50 1.9 grams/kg. At 200 mg/kg it protects the mouse from hypobare hypnoxy at least as well as neclophenoxate. In human therapeutics it may be taken at the daily dose of 50 to 1000 mg/kg.

Product 30: DL 50 – 2.3 g/kg. The Randall-Selito test shows that the product has analgesic and anti-inflammatory properties. On the strain test causing gastric ulcer in the rate, the compound protects notably. It also protects in vitro platelet aggregation caused by collagen, 50% better than aspirin. In human therapeutics it may be used as anti-inflammatory analgesic and in the in depth treatment of cardiovascular seizures.

Product 5: DL 0 – above 5 grams/kg. It is a very active mucolytic according to the Quevauvillier and Eichler tests, which consists of measuring the volume of the bronchial secretions in the anesthetized guinea pig which was subjected to an intragastric injection of physiological liquid. It also has trophic properties for skin and hair and its taste is pleasant, contrary to that of acetyl-ADT for example. In man it may be used for restoring injured mucous, bronchial ones in particularl, at daily doses from 100 to 2500 mg/day.

Product 22: DL 50 – 2.15 mg/kg. sub-chronical treatment in the rat during 16 days at 500 mg/kg, proving the innocuousness of the treatment. According to the Quevauvillier test, the product is a good mucolytic, however, slightly inferior to Product 5. It is usable in pneumology in man at daily doses of 100 to 1000 mg/day.

Product 40: DL 0 higher than 3 g/kg. The product is a vitamin P factor comparable to diethyl amine chromone-2 carboxylate.

I claim:

1. A compound having the formula:

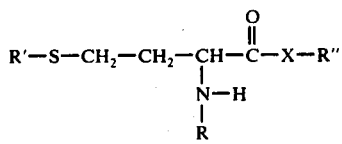

wherein
X is oxygen;
R and R' are each selected from the group consisting of p-chlorophenoxy-2-isobutyryl, pivaloyl, m-fluorobenzoyl, trimethoxy-3,4,5 benzoyl, succinoyl, p-chlorophenoxy acetyl, salicyloyl, acetyl-salicyloyl, acetyl, benzoyl, propionyl; and,
R" is hydrogen or $C_1$ to $C_4$ alkyl.

2. A compound as defined in claim 1 wherein R" is hydrogen.

3. A compound as defined in claim 1 wherein R" is $C_1$ to $C_4$ alkyl.

4. N,S-dibenzoyl homocystein and its salts.

5. N,S-diacetylhomocystein and its salts.